United States Patent [19]

Boron

[11] Patent Number: 4,565,101

[45] Date of Patent: Jan. 21, 1986

[54] MOLTEN METAL PIN SAMPLER

[75] Inventor: Joseph J. Boron, Medina, Ohio

[73] Assignee: Midwest Instrument Co., Inc., Hartland, Wis.

[21] Appl. No.: 543,412

[22] Filed: Oct. 19, 1983

[51] Int. Cl.⁴ ............................................. G01N 1/18
[52] U.S. Cl. ............................. 73/864.57; 73/DIG. 9
[58] Field of Search .................. 73/864.53–864.59, 73/DIG. 9

[56] References Cited

U.S. PATENT DOCUMENTS

| | | | |
|---|---|---|---|
| 3,646,816 | 3/1972 | Hance et al. | 73/DIG. 9 X |
| 3,685,359 | 8/1972 | Boron | 73/DIG. 9 X |
| 4,116,070 | 9/1978 | Falk | 73/864.57 |
| 4,120,204 | 10/1978 | Cure | 73/864.57 |
| 4,140,019 | 2/1979 | Falk | 73/864.57 |

Primary Examiner—Charles Hart
Attorney, Agent, or Firm—Fuller, House & Hohenfeldt

[57] ABSTRACT

A molten metal sampler for obtaining pin samples has mold halves formed from foundry sand with fused quartz tubes located in mold recesses to form the samples. Passages are provided for side filling and end fillings and a bath heat sensor can also be employed.

2 Claims, 8 Drawing Figures

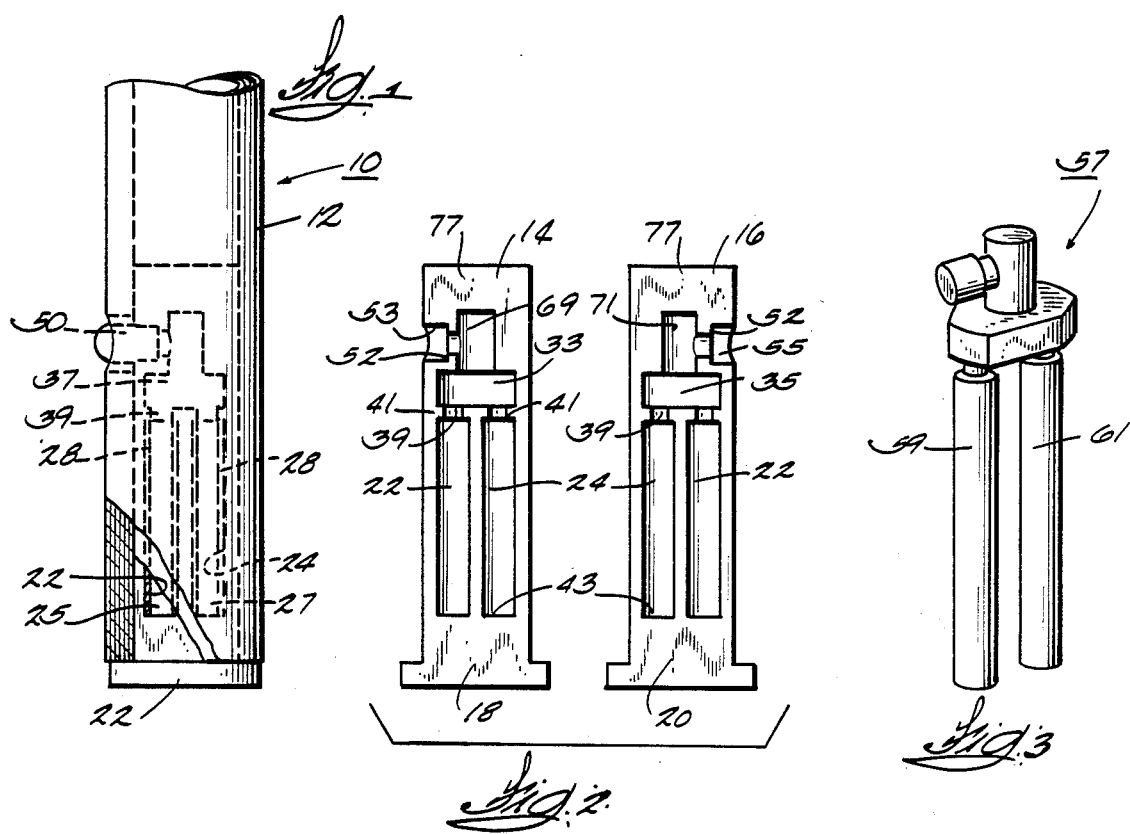
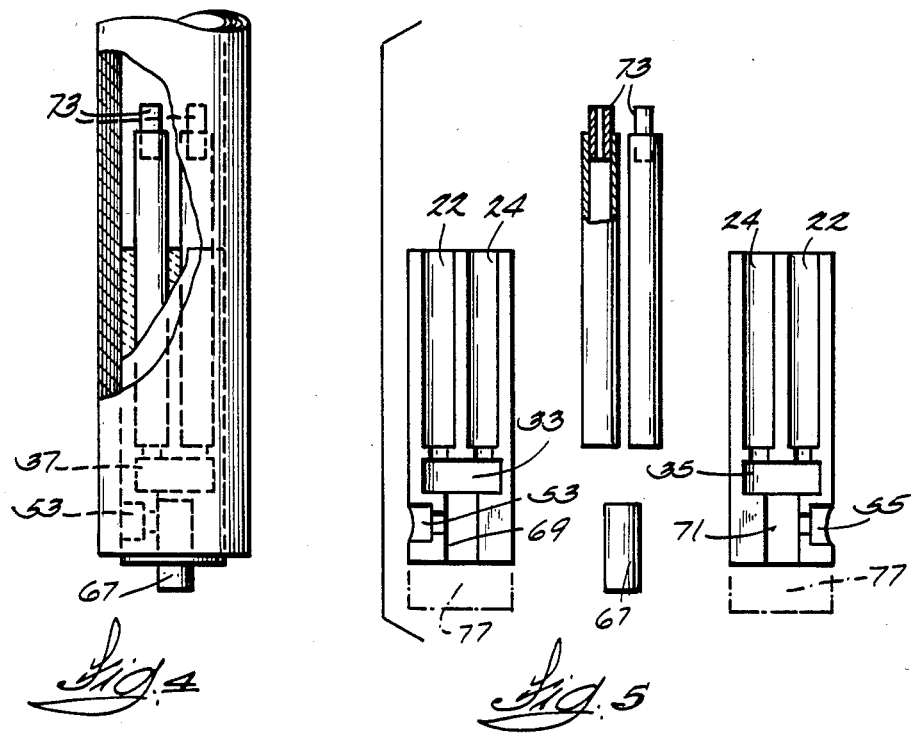

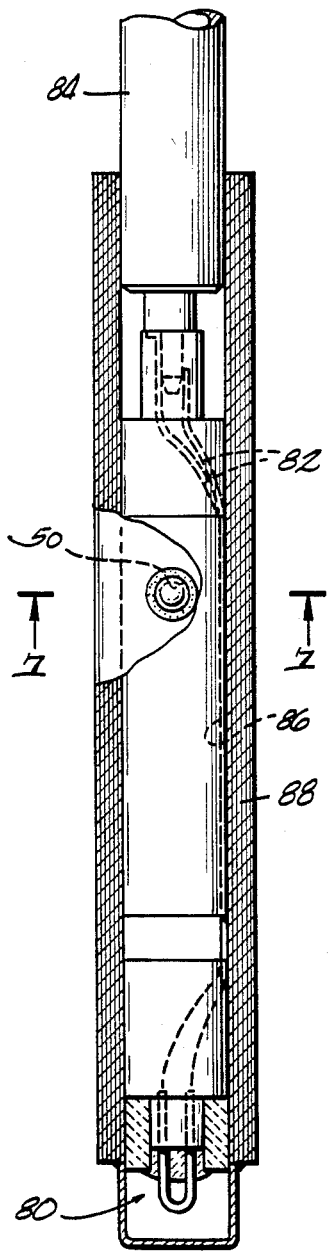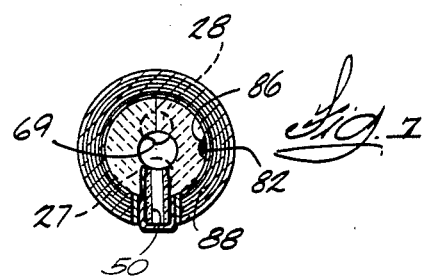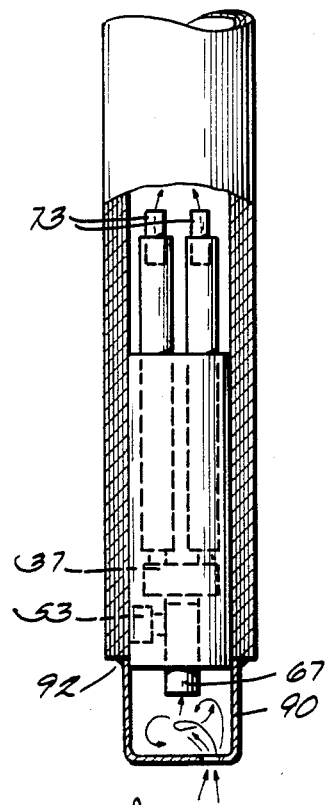

MOLTEN METAL PIN SAMPLER

BACKGROUND OF THE INVENTION

In particular fields of molten metal sampling, only pin samples are required and disc or other shaped samplers are not required. Accordingly in this field low cost samplers which provide only pin samples are desired.

SUMMARY OF THE INVENTION

The invention provides a low cost molten metal pin sampler in which the molds are provided by fused quartz pin tubes, and the tubes are positively positioned in recesses in opposed halves which are formed from foundry sand. The fill passages, and a mixing chamber are all provided by recesses molded into the foundry sand. The mold halves are easily modified or machined to provide adaptability for a wide range of samplers.

Further objects, advantages and features of the invention will become apparent from the disclosure.

DESCRIPTION OF THE DRAWINGS

FIG. 1 is a fragmentary sectional view of one embodiment of the pin sampler of the invention.

FIG. 2 shows the opposed mold halves shown in the sampler of FIG. 1.

FIG. 3 is a sample obtained with the sampler illustrated in FIG. 1.

FIG. 4 is a fragmentary sectional view of a modified embodiment employing mold halves similar to those illustrated in FIG. 2 with modifications for end filling.

FIG. 5 is an exploded view of the parts shown in FIG. 4.

FIG. 6 is a fragmentary side elevational view of a sampler such as illustrated in FIG. 1, including a thermocouple assembly for measuring bath temperature.

FIG. 7 is a sectional view along lines 7—7 of FIG. 7.

FIG. 8 is a fragmentary sectional view of a sampler including an exterior mixing chamber.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

In the drawings, a molten metal sampler 10 includes a paperboard sleeve 12 which carries mold halves 14 and 16 in assembly. The mold halves 14 and 16 are each provided with semi-cylindrical shoulders or flanges 18 and 20 which cooperate to provide a circular disc 22 when they are assembled. Each semi-cylindrical body portion contains recesses 22 and 24 which, when assembled, provide a cylindrical cavity 25 and 27 for fused quartz pin sample mold tubes 28 which are positively positioned in the recesses during assembly and use.

Each mold half 14 andd 16 also includes a semi-cylindrical recess 33 and 35 which provide a common cylindrical mixing chamber 37 when the mold halves are assembled for each of the pin sample tubes 28. Short passages 39 afford communication between the chamber 37 (FIG. 1) and the pin sample tubes 28. Shoulders 41 position the fill tubes in place against the bottom 43 of the recesses 22, 24. A quartz fill tube 50 can be employed and seated against a shoulder 52 in the inlet passage recesses 53 and 55 to provide a side entry port for filling the sampler.

FIG. 3 shows the sample 57 obtained with the sampler configuration illustrated in FIG. 1 with pin samples 59 and 61, which are easily separated for chemical analysis.

FIGS. 4, 5 illustrate a modified form of sampler arranged for end filling and in which the flanges 18 and 20 have been removed and the mold halves inverted and provided with a metal or fill tube 67 located in recesses 69 and 71 of the mold halves. The portions 77 of the molds at the end of the recesses 69, 71 have been removed so that the tubes 67 can be inserted. The fill tube 67 closes off the side entry port provided by recesses 53 and 55 and provides direct communication with the chamber 37. The pin sample tubes may be provided with paper vents 73 which provide an escape of air but prevent outflow of metal as the pin sample tubes are filling.

FIG. 6 shows a sampler similar to FIG. 1 with a side entry port and a bath thermocouple assembly 80. The lead wires 82, which communicate with the theremocouple assembly and an electrical connector head 84, are located in a recess 86 machined in one of the mold halves. The recess 86 is outwardly open. The cardboard sleeve 88 maintains the wires in the recess.

FIG. 8 shows a further modified embodiment of the sampler shown in FIG. 4 including a mixing chamber cup 90 which can be anchored in the cardboard sleeve with refractory cement 92.

I claim:

1. A molten metal sampler for pin samples which is adaptable for both a side entry filling mode or an end filling mode comprises two opposed mold halves, said mold halves being formed from thermosetting foundry sand, each of said mold halves including integrally formed recesses including wall means defining a pair of spaced axially extending recesses, wall means defining a portion of a mixing chamber at the ends of said recesses, with said mixing chamber having an inlet and outlet with said outlet communicating with said pair of axially extending recesses, a wall means defining a longitudinally extending passage communicating with said mixing chamber, inlet and end wall means closing the remote end of said longitudinal passage, and wall means defining a transverse fill passage communicating with said longitudinal recess at a point intermediate the ends of said longitudinally extending passage, a fused quartz fill tube in said longitudinal passage in sealing fit blocking entry of molten metal through said transverse fill passage when said sampler is used in said end filling mode, said mold halves when assembled providing two parallel spaced apertures and fused quartz pin sample molds positively positioned within said apertures and said remote end of said longitudinal passage being removable to enable communication of said passage through the end of said sampler for the end filling mode.

2. A sampler in accordance with claim 1 including laterally extending flange portions projecting from each of said mold halves and a paperboard tube surrounding said mold halves and seated on said flange portion.

* * * * *